United States Patent [19]
Wakamatsu

[11] Patent Number: 5,666,058
[45] Date of Patent: Sep. 9, 1997

[54] CORRECTION METHOD FOR AN ELECTROMAGNETIC INDUCTION-TYPE PROBE

[75] Inventor: Hideki Wakamatsu, Hyogo, Japan

[73] Assignee: Hewlett-Packard Company, Palo Alto, Calif.

[21] Appl. No.: 579,181

[22] Filed: Dec. 27, 1995

[30] Foreign Application Priority Data

Dec. 29, 1994 [JP] Japan ................................. 6-338611

[51] Int. Cl.$^6$ ..................... G01N 27/02; G01R 27/00; G01R 35/00
[52] U.S. Cl. ........................................ 324/445; 324/601
[58] Field of Search ................................ 324/445, 439, 324/601

[56] References Cited

U.S. PATENT DOCUMENTS

| | | | |
|---|---|---|---|
| 3,151,293 | 9/1964 | Blake et al. | 324/445 |
| 3,389,332 | 6/1968 | Ketcham | 324/445 |
| 3,510,761 | 5/1970 | Brown | 324/445 |
| 5,003,267 | 3/1991 | Coleman | 324/445 |
| 5,268,642 | 12/1993 | Uchidomi | 324/445 |
| 5,341,102 | 8/1994 | Akiyama et al. | 324/601 |

FOREIGN PATENT DOCUMENTS 6172023   6/1994   Japan.

*Primary Examiner*—Kenneth A. Wieder
*Assistant Examiner*—Diep Do

[57] ABSTRACT

A method is used which reduces measurement errors, especially of permittivity, which result when electromagnetic induction-type probes measure electrical properties of solutions. Part of the electromagnetic induction current, which the electromagnetic induction-type probe tries to induce in the test solution, flows in the stray capacitance, which is formed by the dielectric in the probe. This partial current reduces the current that is linked to the current detector transformer, and affects the measured value of the electrostatic capacity component, i.e., the permittivity, of the test solution. This phenomenon is modeled and is expressed by a distributed constant circuit which is simplified to a T-shaped 2-terminal pair equivalent circuit. A correction equation that corrects the errors due to the aforementioned currents is obtained by means of this simplified equivalent circuit, and the measurement errors are reduced. Co is the probe's stray capacitance and is evaluated by substituting the correction equation for the measured value of a standard solution. By this means, measurement errors can be reduced to 1/10 of their uncorrected value.

3 Claims, 6 Drawing Sheets

Z: LOOP IMPEDANCE OF SOLUTION

Z: LOOP IMPEDANCE OF SOLUTION

CORRECTION METHOD FOR AN ELECTROMAGNETIC INDUCTION-TYPE PROBE

FIELD OF THE INVENTION

This invention concerns, in general, an impedance measurement device; and in particular, it concerns an error correction method for an electromagnetic induction-type probe, which is used in the field of measuring electrical properties for quantitative research of, testing, and control of the structures of colloidal substances.

BACKGROUND OF THE INVENTION

Colloids are disperse systems consisting of fine particles of the dispersoid and a continuous-phase dispersion medium; the dispersoid and the dispersion medium are not uniformly mixed. As a method for evaluating the form of this kind of non-uniform structure, electrical properties are measured, such as the conductivity, permittivity, etc. In recent years, in particular, methods for measuring permittivity using impedance measurements have been studied.

The Applicant proposed an electromagnetic induction-type conductivity and permittivity meter as an effective means for measuring the capacitance of solutions with large conductivities, i.e., their permittivities, in Japanese Patent Application No. 6[1994]-172023. This device solves the problem of errors due to electrode polarization, which is a disadvantage of the conventional electrode type, and is able to perform accurate measurements of permittivity without the effect of the conductivity. In that application, a probe structure and a simple correction method (calibration method) were proposed. The present invention is a proposal for improving the calibration method and reducing errors still further.

The permittivity measurement of the electromagnetic induction-type disclosed in Japanese Patent Application No. 6[1994]-172023 removes the effects of changes in conductivity of the solution on the measured permittivity value to a much greater extent, when compared to the electrode mode of measuring permittivity. This is because the electrode interfacial polarization is eliminated, principle. However, the following problem arises when the sensitivity multiplier (the so-called cell constant in the current equation) is corrected on the basis of the conductivity.

FIG. 2 shows an example of the expression of the true value and the measured value of the permittivity of an aqueous solution with respect to changes in frequency, using the conductivity of the solution as a parameter. The problem is that the measured value of the permittivity shows a lower value than the true one, and the measured value of the permittivity is affected by changes in conductivity. The magnitude of this error may be more than 30% in some cases. Moreover, when a solution is measured, in which the product of the permittivity and the angular frequency is almost equal to the conductivity in the measurement frequency range, the measured permittivity value is also changed by changes in frequency, as shown in the figure.

Before discussing the cause of this problem, we shall explain the electromagnetic induction-type probe of the prior art. FIGS. 6, 7, and 8 show first, second, and third actual examples, respectively, of the electromagnetic induction-type probe proposed in Japanese Patent Application No. 6[1994]-172023. Furthermore, the elements in each figure with the same functions are given the same numbers. These elements form the following structure. The main frame of impedance measuring instrument 1 has a signal source 2, a resistance 3, a voltmeter 4, and an ammeter 5. Electromagnetic induction-type probe 8 has a primary core 10, a primary coil 11 and secondary core 12, a secondary coil 13, and a shield 14 with a gap 15; these elements are contained in an outer resin mold 9. Moreover, impedance measuring instrument 1 and probe 8 are connected by coaxial cables 6 and 7. Primary core 10 of the probe off FIG. 7 has a hole 16 running through it, and the probe of FIG. 8 has a balun 18 and a shunt 17. The equivalent circuit of the balun is shown by 19.

Simplified versions of the structures of FIGS. 6, 7 and 8 are as shown in FIG. 3. In this figure, the cross sections of the primary and secondary transformers and the inputs and outputs of the transformers are shown. When the excitation current supplied from signal source 2 flows to primary coil 11 and primary toroidal core 10 is excited, a concentric electrical field 31 is produced, the center of which is the center of the cross section of primary toroidal core 10. When the probe is dipped into the solution, the current surrounding the probe flows in the solution, due to electrical field 31, and as a result, secondary toroidal core 12 is excited and a current flows in secondary coil 13, producing a value on ammeter 5. From the vector ratio of this current value and the voltage applied to primary coil 11, which is measured by voltmeter 4, the conductance component and the susceptance component of the solution can be obtained.

Since the equivalent circuit of the solution can be expressed as parallel circuits of the resistance, which is determined by the conductivity of the solution, and the capacitance which is determined by the permittivity, method is performed by which the permittivity is obtained by a calculation process from the aforementioned susceptance component, i.e., capacitance component, of the solution.

FIG. 4 shows the current that flows due to the electrical field of the primary toroidal core. In the figure, cross sections of the primary and secondary transformers and the outer resin mold of the probe are drawn as constituent elements of the probe. The current that flows due to the electrical field of the primary toroidal core 10 includes: a current 32 that flows only in the solution, and a current 33 that flows from the solution, through the probe, and back into the current. Since the probe is filled with an insulator (not shown in the figure) which insulates the conductors, there is a stray capacitance (due to the dielectric effect of the insulator) in which a current flows. Furthermore, since the resistance value of the insulator is extremely high, the current that flows in the resistance component of the insulator can be ignored. The current 33 that flows in this stray capacitance is linked to secondary core 12 and reduces the current that would be expected to flow. As a result, roughly speaking, the permittivity value measured is smaller than the true value.

As mentioned above, the fact that the measured permittivity value is lower than the true value and the measured permittivity value is affected by changes in the conductivity, are both caused by the stray capacitance in the probe.

Moreover, it is extremely difficult to make the value of this stray capacitance small enough so that its effects can be ignored, and doing so places many restrictions on the structure of the probe.

OBJECT OF INVENTION

This invention's object is to overcome the prior art problem of obtaining a permittivity measurement that is smaller than the true value. Thus, the principle object of the invention is to provide an electromagnetic induction-type probe that can measure permittivity with high accuracy.

SUMMARY OF THE INVENTION

A method is used which reduces measurement errors, especially of permittivity, which result when electromagnetic induction-type probes measure electrical properties of solutions. Part of the electromagnetic induction current, which the electromagnetic induction-type probe tries to induce in the test solution, flows in the stray capacitance, which is formed by the dielectric in the probe. This partial current reduces the current that is linked to the current detector transformer, and affects the measured value of the electrostatic capacity component, i.e., the permittivity, of the test solution. This phenomenon is modeled and is expressed by a distributed constant circuit which is simplified to a T-shaped 2-terminal pair equivalent circuit. A correction equation that corrects the errors due to the aforementioned currents is obtained by means of this simplified equivalent circuit, and the measurement errors are reduced. Co is the probe's stray capacitance and is evaluated by substituting the correction equation for the measured value of a standard solution. By this means, measurement errors can be reduced to 1/10 of their uncorrected value.

EXPLANATION OF SYMBOLS

1: Impedance measuring instrument main frame;
2: Signal source;
3: Resistance;
4: Voltmeter;
5: Ammeter;
6: Coaxial cable;
7: Coaxial cable;
8: Electromagnetic induction-type probe;
9: Outer resin molding;
10 Primary toroidal core;
11: Primary coil;
12: Secondary toroidal core;
13: Secondary coil;
14: Shield;
15: Gap;
16: Hole running through core;
17: Shunt;
18: Balun;
19: Equivalent circuit of balun;
31: Electrical field excited by the primary toroidal core;
32: Current flowing through solution only;
33: Current flowing through both the solution and the probe;
Co: Equivalent stray capacitance in probe;
Zo: Impedance value of equivalent stray capacitance in probe;
Z: Loop impedance of solution;
Zm: Measured value of loop impedance of solution.

DETAILED DESCRIPTION OF THE INVENTION

Figure 4:
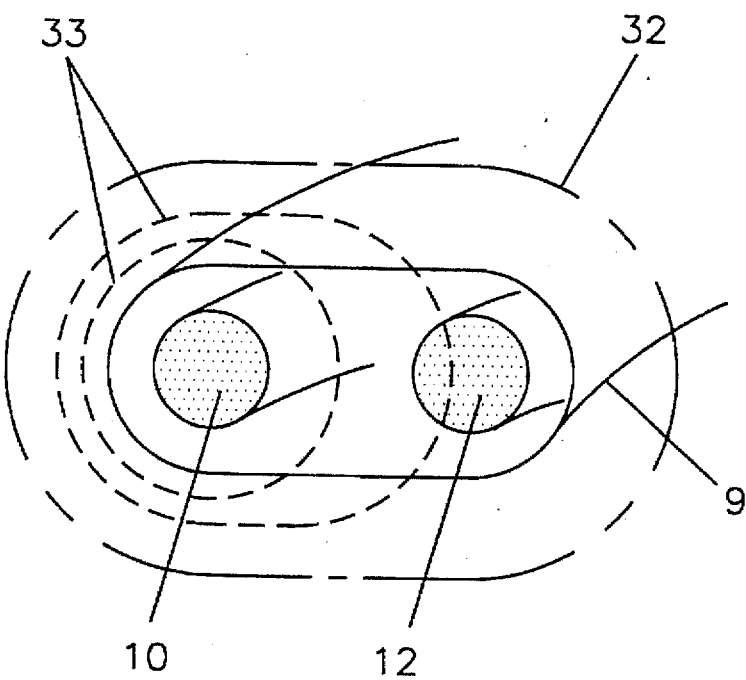
FIG. 4 is a diagram showing current pathways of a probe of the prior art.
Figure 5:
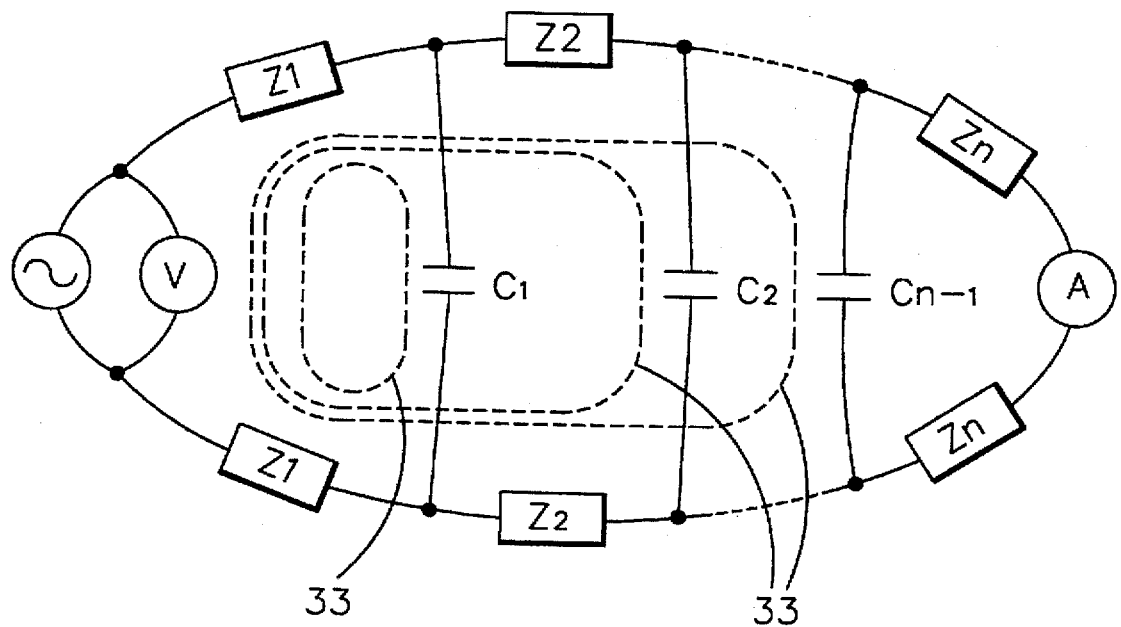
FIG. 5 is a diagram showing a distributed constant equivalent circuit of the current pathways.
Figure 6:
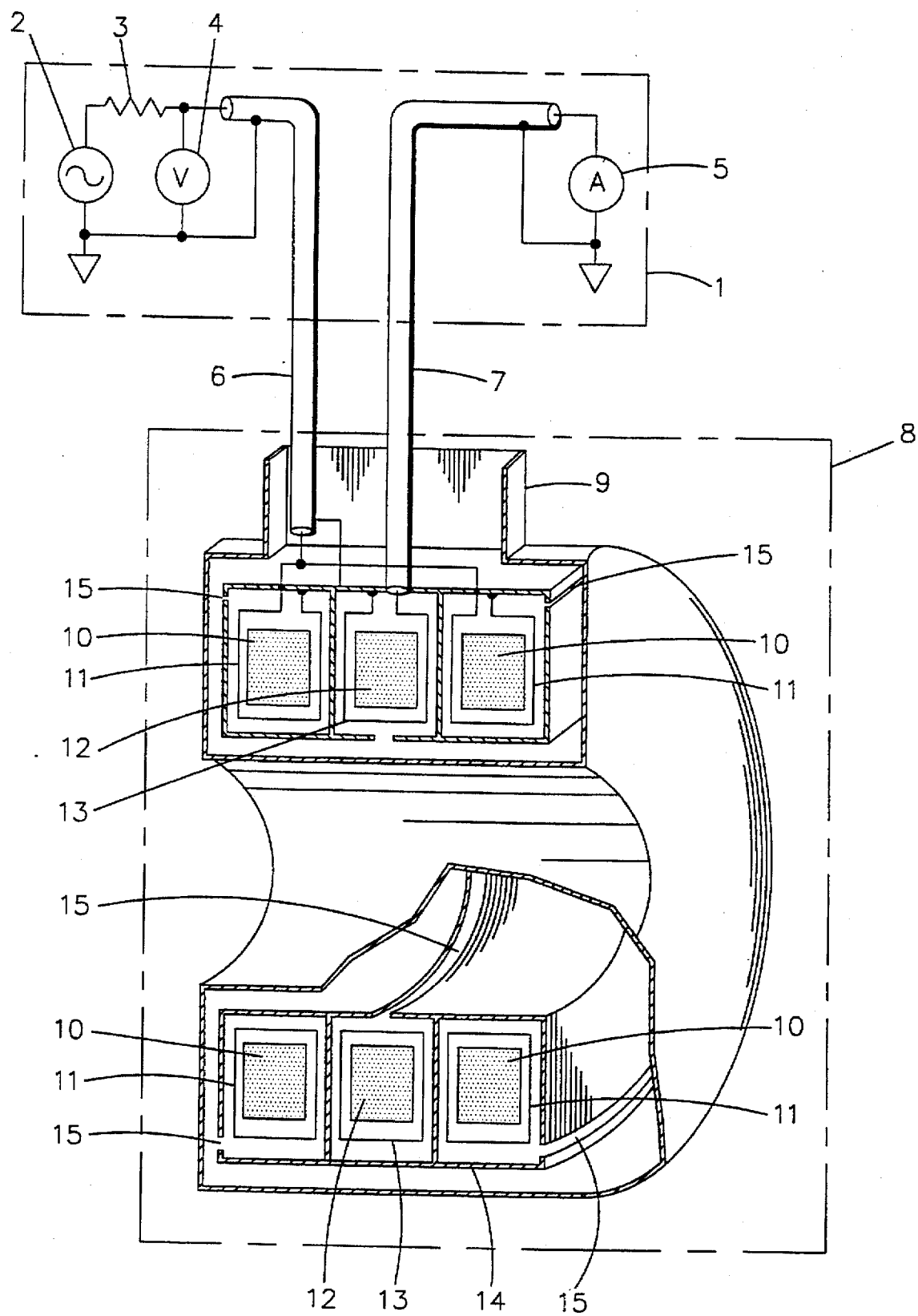
FIG. 6 is a diagram showing a first example of a probe of the prior art.
Figure 7:
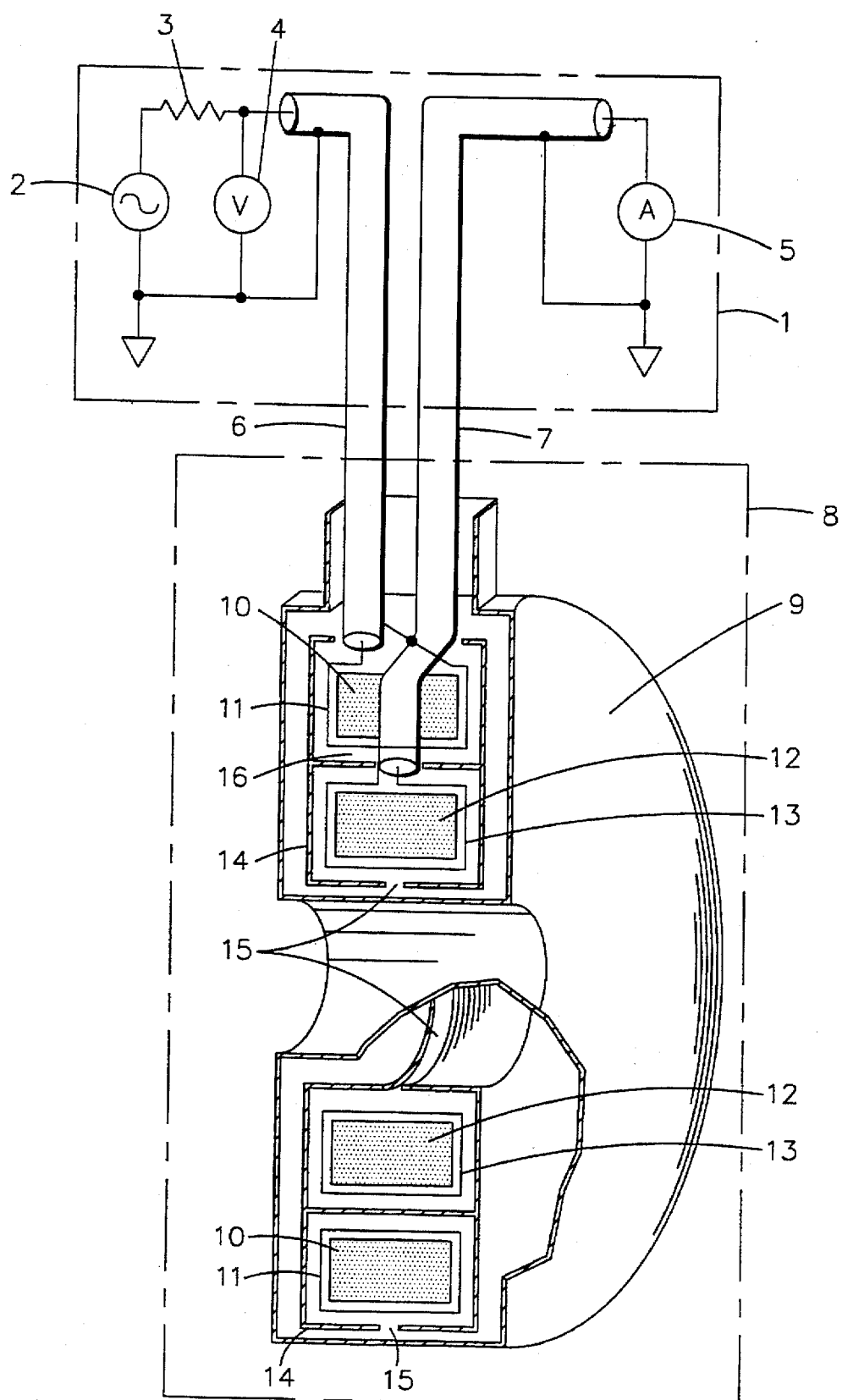
FIG. 7 is a diagram showing a second example of a probe of the prior art.
Figure 8:
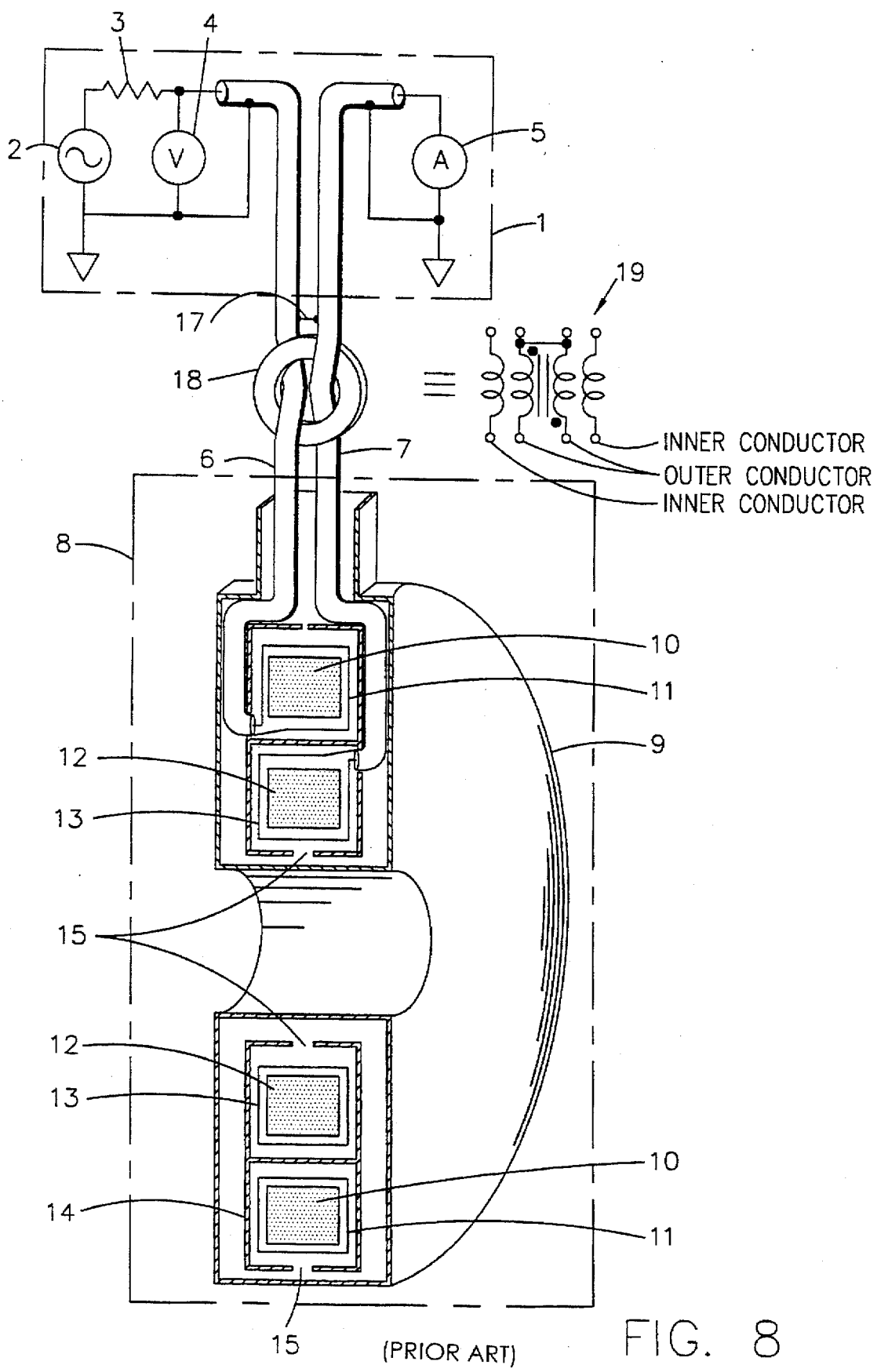
FIG. 8 is a diagram showing a third example of a probe of the prior art.

The current pathway inside and outside the probe is expressed by an equivalent circuit with distributed constants, as shown in FIG. 5. The Z1–Zn notations in the figure show the distribution of the impedance of the solution; and their sum is the loop impedance of the solution. Here, the term "loop impedance" refers to the total impedance along the pathway of the closed-path current (current 32 of FIG. 4) produced by electromagnetic induction of the electromagnetic induction-type probe. The c1–Cn-1 notations of FIG. 5 show the distribution of stray capacitance in the probe. Dotted lines 33 show the current passing from the solution into the probe, due to the distribution of the loop currents.

Figure 1:
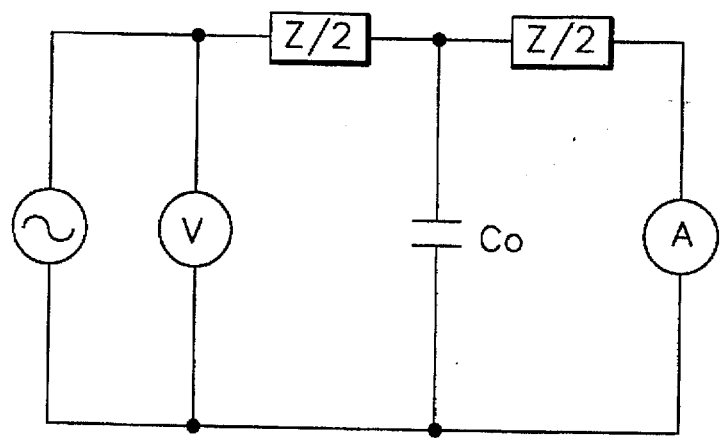
FIG. 1 is a diagram showing an equivalent circuit of current pathways used in an actual example of this invention.
Figure 1:
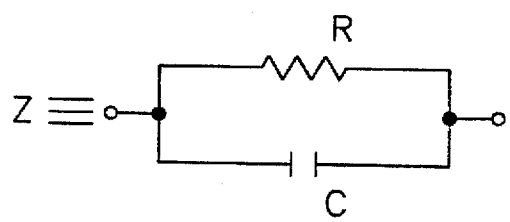

This invention performs corrections by modeling, as a first approximation, the equivalent circuit of this distributed circuit by a T-shaped 2-terminal pair circuit, as shown in FIG. 1. The sum of the impedances of the series elements of this circuit is the loop complex impedance Z of the solution, and the capacitance Co, which is a parallel element and is the equivalent stray capacitance in the probe.

When the relationship between the loop complex impedance Z of the solution and the impedance value Zm actually measured is obtained from the equivalent circuit of FIG. 1, the result is equation (1) below.

$$Zm = Z(1 + Z/4Zo) \quad (1)$$

where: $Zo = 1/j\omega Co$

In an impedance measurement instrument, as is known, a simple, accurate, and stable calibration can be performed by using three known impedances, i.e., "OPEN," "SHORT," and "LOAD." For this calibration method, see Japanese Patent Application Nos. 5 [1993]-85545 and 5 [1993]-352215.

Applicant has proposed, in Japanese Patent Application No. 6[1994]-172023, a means for applying the calibration method using the aforementioned 3 known impedances (3-term error correction method) to the calibration of measurement instruments using electromagnetic induction-type probes. If Co is known, the correction equation derived from the reverse calculation of equation (1) (i.e. derivation of equation 2 from equation 1) can be substituted for the measured value of a test solution measured using the probe that has been calibrated by this calibration means, and the true value of the impedance of the solution can be obtained.

$$Z = 2Zm/(1 + [1 + Zm/Zo]^{0.5}) \quad (2)$$

Equation (2) above is the correction equation. Since Z has the following relationships with the permittivity $\epsilon$ and the conductivity $\kappa$ of the solution, the permittivity and conductivity can be obtained from the measured value of the impedance.

$$\epsilon = Kc \cdot \text{Imag}(1/Z)/\omega [F/m]$$

$$\kappa = Kc \cdot \text{Real}(1/Z)[S/m]$$

"where: F/M is farads per meter where: S/M is siemens per meter".

The Kc in the equation above is called the cell constant; it is a constant intrinsic to the shape of the probe, which converts the impedance of the solution to the permittivity $\epsilon$ and the conductivity $\kappa$. Moreover, $\omega$ is the angular frequency of the measurement signal. The cell constant, as mentioned in Japanese Patent Application No. 6[1994]-172023, is an unchanging multiplier that can be obtained by a one-time operation in the development stage of the probe.

In the same manner, the equivalent stray capacitance Co in the probe is an unchanging constant that can be obtained by a one-time operation in the development stage of the probe. Since Co is determined by the material and structure of the probe, the variations in these factors can be controlled in such a way that the individual differences among probes can be ignored.

The Co value is determined by the following method. First, a standard solution with a known permittivity (e.g., water, with a specific permittivity of 78.3) is measured, and the permittivity is obtained by performing the correction using correction equation (2). The value of is obtained in such a way that the measured permittivity value agrees with the aforementioned known value. That is, since Kc is determined from the conductivity of a solution with a known conductivity, Co is determined from the permittivity of a solution with a known permittivity.

Here, doubts may arise as to whether the conductivity and permittivity, i.e., Kc and Co, may interfere, and may be difficult to determine independently. However, in the equivalent circuit of FIG. 1, C is >Co or approximately=Co, and the effect of Co on the measured conductivity value (i.e., the measured value of the resistance component) is sufficiently small. This condition is established in ordinary probe structures, if the standard solution is made an aqueous solution.

As mentioned above, the differences in individual probes with respect to the cell constant Kc and the equivalent stray capacitance Co are ordinarily small and these values can be obtained once and for all in the product development stage, but it is also possible to calibrate these values at the time the probe is used. This may be done by means of the aforementioned Co value determination method, i.e., by preparing a standard solution with known permittivity and conductivity (e.g., an aqueous solution of potassium chloride). It may be set so that the measured value of the conductivity and the value of the standard solution agree, as with Kc and Co. If the calibration is performed at the time of use, one can make corrections in response to changes in the cell constant KC and the equivalent stray capacitance Co due to changes over time in the probe mold material.

Figure 2:
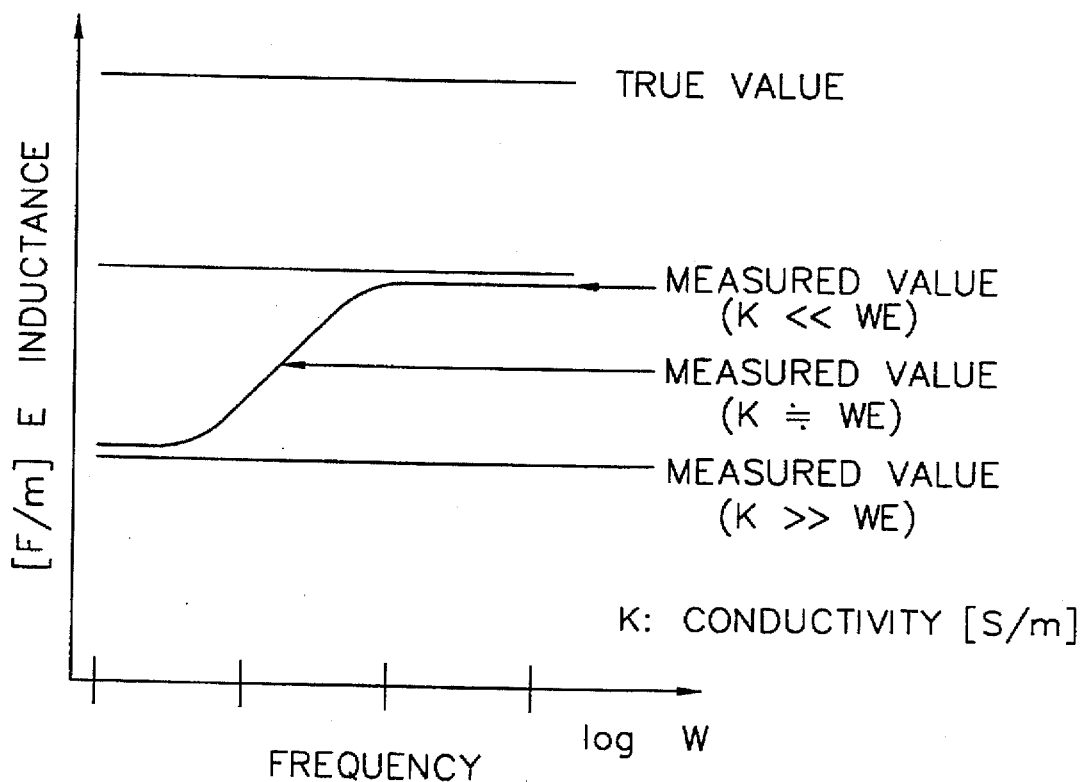
FIG. 2 is a diagram showing the tendency of the measured permittivity value, as measured by the prior art.
Figure 3:
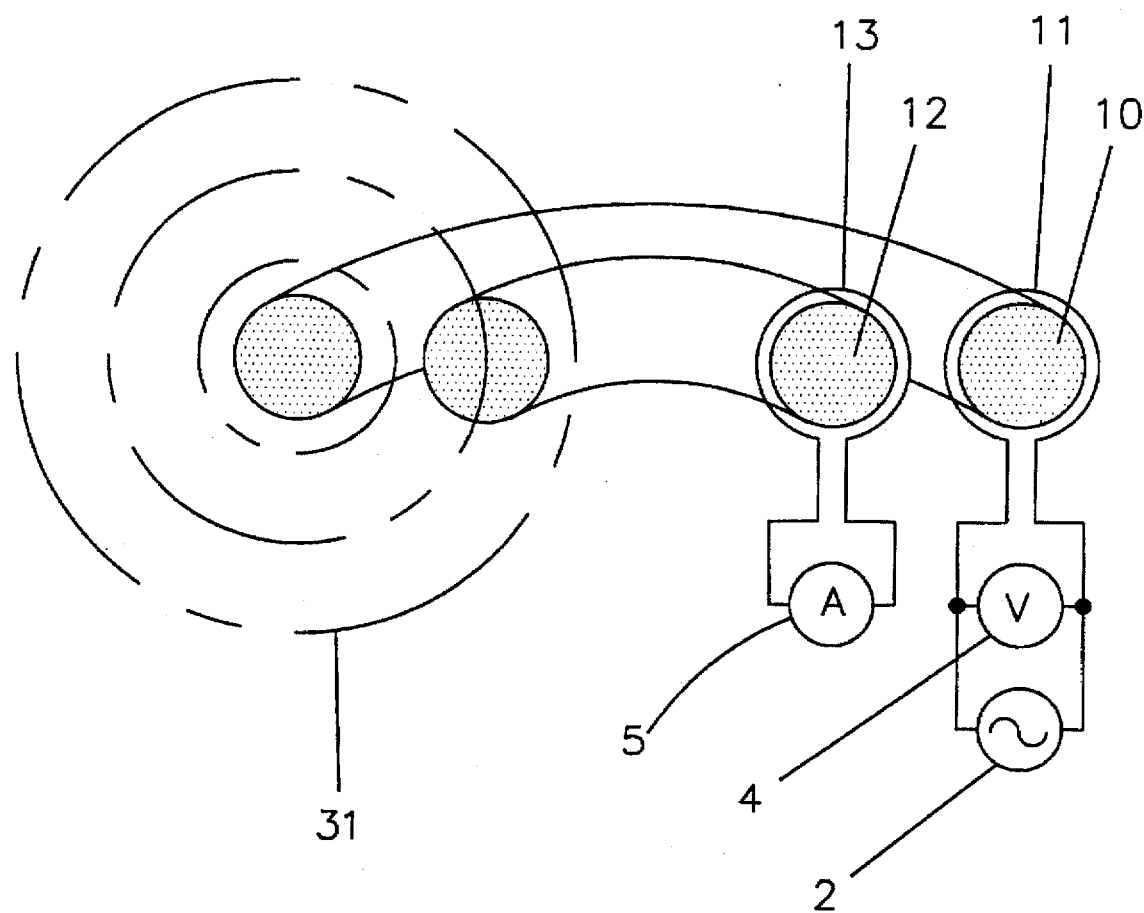
FIG. 3 is a schematic diagram of the structure of the probe of the prior art.

By means of this invention, as mentioned above, the pathway through which the current produced by the electromagnetic induction, which is the original distributed constant circuit, can be modeled by the lumped constant equivalent circuit of FIG. 1, and a correction can be achieved by a simple correction method. For example, the magnitude of the error, which was 30% or more in FIG. 2, was reduced to 3% or less.

An actual example of this invention was shown above, but this invention is not limited to the style, forms of parts, arrangement of parts, or other aspects shown in this example. If desired, modifications in the structure of the invention are allowed, as long as they do not conflict with its essence.

Effectiveness of Invention

An improvement is shown for the calibration method of electromagnetic induction-type probes proposed in Japanese Patent Application No. 6 [1994]-172023. According to the invention, permittivities can be measured with high accuracy and in a stable manner, removing the effect of the stray capacitance in the probe, and without dependence on changes in the conductivity; thus, this invention has practical advantages. Conversely, it also makes it possible to reduce the limitations on the structure of the probe, which are otherwise needed to make the stray capacitance smaller.

I claim:

1. A correction method comprising the steps of:
   a. measuring electrical properties of a solution by employing an electromagnetic induction-type probe;
   b. measuring electrical properties of a standard solution having a known permittivity by employing said electromagnetic induction-type probe;
   c. approximating current pathways both inside and outside said probe through use of an electrical equivalent circuit, a value of at least one constituent element of said equivalent circuit obtained from results of said measurement of step (b) and a standard value of at least one parameter of said standard solution; and
   d. correcting a measured value obtained in step (a) by use of said value of said at least one constituent element.

2. The correction method as recited in claim 1, wherein said equivalent circuit is a T-shaped 2-terminal pair circuit which expresses a loop impedance of a solution being measured by a sum of impedances of series elements and parallel elements which represent an equivalent stray capacitance in said probe.

3. A correction method wherein electrical properties of a solution is measured by use of an electromagnetic induction-type probe, said method comprising the steps of:
   a. approximating current pathways both inside and outside the probe by use of a T-shaped 2-terminal pair circuit, which expresses a loop impedance of the solution being measured by a sum of impedances of series circuit elements and an equivalent stray capacitance in said probe by parallel circuit elements;
   b. measuring a standard solution with a known permittivity by use said probe;
   c. obtaining a value of an equivalent stray capacitance of said probe from results of said measuring step (b) and the known permitivity; and
   d. employing said electromagnetic induction-type probe to obtain a measured value of an electrical property of a solution and correcting said measured value by using said value obtained in step (c).

* * * * *